United States Patent [19]
Black et al.

[11] Patent Number: 5,994,371
[45] Date of Patent: Nov. 30, 1999

[54] CARBAMATE DERIVATIVES OF 3-AROYLBENZO[B] THIOPHENES

[75] Inventors: Larry J. Black; Henry U. Bryant, both of Indianapolis; George J. Cullinan, Trafalgar, all of Ind.

[73] Assignee: Eli Lilly and Company, Indianapolis, Ind.

[21] Appl. No.: 08/392,445

[22] Filed: Feb. 22, 1995

Related U.S. Application Data

[63] Continuation of application No. 08/035,121, Mar. 19, 1993, Pat. No. 5,482,949.

[51] Int. Cl.$^6$ ........................ C07D 409/00; A61K 31/445
[52] U.S. Cl. ............................ 514/324; 546/202
[58] Field of Search ............................. 546/202; 514/324

[56] References Cited

U.S. PATENT DOCUMENTS

| | | | |
|---|---|---|---|
| 4,133,814 | 1/1979 | Jones et al. | 260/326.55 |
| 4,418,068 | 11/1983 | Jones | 424/267 |
| 4,729,999 | 3/1988 | Young | 514/727 |
| 4,894,373 | 1/1990 | Young | 514/239.2 |
| 4,970,237 | 11/1990 | Jensen et al. | 514/651 |

FOREIGN PATENT DOCUMENTS 509317  10/1992  European Pat. Off. .

OTHER PUBLICATIONS

Williams, et al., *Journal of Bone and Mineral Research*, 6 (1991).
*FDC Reports*, T&G 11, Mar. 30, 1992.
Jones, et al., *J. Med. Chem.,* 27, 1057–1066 (1984).
Feldmann, et al., *Bone and Mineral*, 7, 245–254 (1989).
"Tamoxifen Trial Restricted", *SCRIP* No. 1702 Mar. 20, 1992, p. 22.
Jordan, et al., *Breast Cancer Research Treatment*, 10: 31–35 (1987).
Beall, et al., *Calcif Tissue Int.,* 36: 123–125 (1984).
Turner, et al., *Journal of Bone and Mineral Research,* 2, No. 5, 449–456 (1987).
Williams, et al., *Bone and Mineral*, 14, 205–220 (1991).
Turner, et al., *Endocrinology,* 122, No. 3, 1146–1150 (1988).
Love, et al., *The New England Journal of Medicine,* 326, No. 13, 852–856 (1992).
Breckenridge, et al., *Lipids,* 22, No. 7, 505–512 (1987).
Lazier, et al., *Biochem. Cell Biol.,* 68, 210–217 (1990).
Lobo, *J. Clin. Endocrinol. Metab.,* 73, No. 5, 925–930 (1991).
Love, et al.,*Ann. Intern. Med.,* 115, No. 11, 860–864 (1991).
Walsh, et al., *N. Engl. J. Med.,* 325, No. 17, 1196–1204 (1991).
Bagdade, et al., *J. Clin. Endocrinol. Metab.,* 70, No. 4, 1132–1135 (1990).
Love, et al., *J. Natl. Cancer Inst.,* 82, No. 16, 1327–1332 (1990).
Teo, et al., *J. Med. Chem.,* 35, 1330–1339 (1992).
Cypriani, et al., *J. Steroid Biochem.,* 31, No. 5, 763–771 (1988).
Cypriani, et al., *Chemical Abstracts,* CA 110: 1189 v, 1989.
Cypriani, et al., *Chemical Abstracts,* 110:69550v, 1989.
American Chemical Society, *Registry,* RN# 63676–25–5.

*Primary Examiner*—Sharon Gibson
*Assistant Examiner*—Catherine Kilby Scalzo
*Attorney, Agent, or Firm*—James J. Sales

[57] ABSTRACT

The present invention relates to sulfonate and carbamate derivatives of 3-aroylbenzo[b]thiophenes, pharmaceutical formulations containing these compounds and methods of using such compounds for inhibiting the loss of bone, lowering serum cholesterol levels and therapeutically treating hormone dependent mammalian breast and uterine carcinoma.

10 Claims, No Drawings

CARBAMATE DERIVATIVES OF 3-AROYLBENZO[B] THIOPHENES

This application is a continuation of application Ser. No. 08/035,121, filed Mar. 19, 1993, now U.S. Pat. No. 5,482,949.

BACKGROUND OF THE INVENTION

The present invention relates to 3-aroylbenzothiophenes, compositions containing those compounds and their use in preventing bone loss, treating hypercholesterolemia and treating hormone dependent mammalian breast and uterine carcinoma.

The mechanism of bone loss is not well understood, but in practical effect, the disorder arises from an imbalance in the formation of new healthy bone and the resorption of old bone, skewed toward a net loss of bone tissue. This bone loss includes a decrease in both mineral content and protein matrix components of the bone, and leads to an increased fracture rate of, predominantly, femoral bones and bones in the forearm and vertebrae. These fractures, in turn, lead to an increase in general morbidity, a marked loss of stature and mobility, and, in many cases, an increase in mortality resulting from complications.

Bone loss occurs in a wide range of subjects, including post-menopausal women, patients who have undergone hysterectomy, patients who are undergoing or have undergone long-term administration of corticosteroids, patients suffering from Cushing's syndrome, and patients having gonadal dysgensis.

Unchecked, bone loss can lead to osteoporosis, a major debilitating disease whose prominent feature is the loss of bone mass (decreased density and enlargement of bone spaces) without a reduction in bone volume, producing porosity and fragility.

One of the most common types of osteoporosis is found in post-menopausal women affecting an estimated 20 to 25 million women in the United States alone. A significant feature of post-menopausal osteoporosis is the large and rapid loss of bone mass due to the cessation of estrogen production by the ovaries. Indeed, data clearly support the ability of estrogens to limit the progression of osteoporotic bone loss, and estrogen replacement is a recognized treatment for post-menopausal osteoporosis in the United States and many other countries.

All mammalian cells require cholesterol as a structural component of their cell membranes and for non-sterol end products. Cholesterol is also required for steroid hormone synthesis. The very property, however, that makes cholesterol useful in the cell membranes, its insolubility in water, also makes it potentially lethal. When cholesterol accumulates in the wrong place, for example within the wall of an artery, it cannot be readily mobilized and its presence leads to the development of an atherosclerotic plaque. Elevated concentrations of serum cholesterol associated with low density lipoproteins have been demonstrated to be a major contributing factor in the development and progression of atherosclerosis.

In mammals, serum lipoprotein is composed of cholesterol together with cholesteryl esters, triglycerides, phospholipids and apoproteins. Serum or plasma lipoprotein is comprised of several fractions. The major fractions or classes of plasma lipoproteins are very low density lipoprotein (VLDL), low density lipoprotein (LDL), intermediate density, lipoprotein (IDL), and high density lipoprotein (HDL). These classes differ from one another in size and density in the relative proportions of triglycerides and cholesteryl esters in the core, and in the nature of the apoproteins on the surface.

In mammals, serum cholesterol is derived from exogenous dietary sources as well as through endogenous synthesis. Endogenous synthesis of cholesterol involves a complex set of enzyme-catalyzed reactions and regulatory mechanisms generally termed the mevalonate pathway. Cells face a complex problem in regulating mevalonate synthesis because cholesterol, the bulk end product of mevalonate metabolism, is derived from plasma low density lipoprotein which enters the cell by receptor-mediated endocytosis, as well as from synthesis within the cell. Each cell must balance these external and internal sources so as to sustain mevalonate synthesis while avoiding sterol over accumulation. This balance is achieved through feedback regulation of at least two sequential enzymes in mevalonate synthesis, 3-hydroxy-3-methylglutaryl coenzyme A (HMG-CoA) synthase and HMG-CoA reductase and also of LDL receptors. In the absence of LDL, mammalian cells maintain high activities of the two enzymes, thereby synthesizing mevalonate for production of cholesterol as well as the non-sterol products. When LDL is present, from exogenous sources, HMG-CoA synthase and reductase activity is repressed and the cells produce smaller amounts of mevalonate for the non-sterol end products.

Abundant evidence indicates that treatment of hyperlipoproteinemia will diminish or prevent atherosclerotic complications. In addition to a diet that maintains a normal body weight and minimizes concentrations of lipids in plasma, therapeutic strategies include elimination of factors that exacerbate hyperlipoproteinemia and the administration of therapeutic agents that lower plasma concentrations of lipoproteins, either by diminishing the production of lipoproteins or by enhancing the efficiency of their removal from plasma.

A promising class of drugs currently available for the treatment of hypercholesterolemia act by inhibiting HMG-CoA reductase, the rate-limiting enzyme of endogenous cholesterol synthesis. Drugs of this class competitively inhibit the activity of the enzyme. Eventually, this lowers the endogenous synthesis of cholesterol and, by normal homeostatic mechanisms, plasma cholesterol is taken up by LDL receptors to restore the intracellular cholesterol balance.

Relative to other cells in the body, liver cells play a critical role in maintaining serum cholesterol homeostasis by both releasing precursors of LDL and through receptor mediated LDL uptake from the serum. In both man and animal models an inverse correlation appears to exist between liver LDL receptors and LDL associated serum cholesterol levels. In general, higher hepatocyte receptor numbers result in lower LDL associated serum cholesterol levels. Cholesterol released into hepatocytes can be stored as cholesterolesters, converted into bile acids and released into the bile duct, or enter into an oxycholesterol pool. It is this oxycholesterol pool that is believed to be involved in end product repression of both the genes of the LDL receptor and enzymes involved in the cholesterol synthetic pathway.

In populations where coronary heart disease is a major health problem, the incidence of the disease is markedly lower in women than in men. This is particularly true in younger age groups, such as men and women between 35 and 44 years of age.

Generally, plasma lipoprotein metabolism is influenced by the circulating concentrations of gonadal steroids. Changes in serum estrogen and androgen concentrations, resulting from alterations in gonadal status or from the administrative of exogenous gonadal steroids are associated with changes in serum lipoprotein levels. The changes effected by estrogens and androgens generally support the proposition that sex differences in lipoproteins are due to hormonal differences between men and women.

The generally accepted relationship between gonadal steroids and plasma lipoproteins is that androgens lower HDL concentrations and increase LDL, thus contributing to the low HDL and high LDL levels observed in men when compared to women. Estrogens are held to have opposite effects on lipoproteins; that is, HDL is raised and LDL is lowered. These sex steroid-induced differences in lipoprotein concentrations are thought to contribute to the lower incidence of cardiovascular disease in women compared to men. After the menopause, the protective effect of estrogens in women is lost and the incidence of cardiovascular disease increases towards the male levels. Postmenopausal women who take estrogens generally have lower rates of cardiovascular disease than women of a similar age who do not. Estrogen, particularly when taken orally, lowers plasma levels of LDL and raises those of HDL.

The mechanisms by which estrogen lowers levels of LDL and raises those of HDL are not known. In general, changes in the plasma concentration of a lipoprotein result from changes in the rate of its synthesis or the rate of its catabolism. For example, estrogen may lower LDL levels by increasing the clearance of LDL from plasma, since estrogen increases the number of hepatic LDL receptors in animals.

Tamoxifen (1-p-β-dimethylaminoethoxyphenyl-trans-1, 2-diphenyl-but-1-ene), is a well-known antiestrogen compound having activity against mammalian breast carcinoma. See *The Merck Index*, 11th Ed., 1430 (1989). Furthermore, tamoxifen analogues also have antiestrogenic activity, including activity against mammalian breast carcinoma (U.S. Pat. No. 4,623,660). Numerous other compounds have similarly shown antiestrogenic activity resulting in suppression of mammalian breast tumor growth. For example, 2-phenyl-3-aroylbenzothiophenes and 2-phenyl-3-aroylbenzothiophene-1-oxides were disclosed in U.S. Pat. No. 4,133,814; 3-phenyl-4-aroyl-1,2-dihydronaphthalenes and 1-aroyl-2-phenylnaphthalenes were described in U.S. Pat. No. 4,230,862; and 6-hydroxy-2-(4-hydroxyphenyl)-3-[4-(2-piperidinoethoxy)benzoyl]benzo[b]thiophene was taught in U.S. Pat. No. 4,418,068.

Although estrogens have beneficial effects on bone and serum lipids, given even at very low levels, long-term estrogen therapy has been implicated in a variety of disorders, including an increase in the risk of uterine and breast cancer, causing many women to avoid this treatment. Recently suggested therapeutic regimens, which seek to lessen the cancer risk, such as administering combinations of progestogen and estrogen, cause the patient to experience regular withdrawal bleeding, which is unacceptable to most older women. Concerns over the significant undesirable effects associated with estrogen therapy, and the limited ability of estrogens to reverse existing bone loss, support the need to develop alternative therapy for bone loss, hypercholesterolemia and hormone dependent mammalian breast and uterine carcinoma that generates the desirable effects but does not cause undesirable effects.

Attempts to fill this need by the use of compounds commonly known as antiestrogens, which interact with the estrogen receptor, have had limited success, perhaps due to the fact that these compounds generally display a mixed agonist/antagonist effect. That is, although these compounds can antagonize estrogen interaction with the receptor, the compounds themselves may cause estrogenic responses in those tissues having estrogen receptors. Therefore, some antiestrogens are subject to the same adverse effects associated with estrogen therapy.

The present invention provides compounds, pharmaceutical formulations containing said compounds and methods for inhibiting bone loss, treating hypercholesterolemia and treating hormone dependent mammalian breast and uterine carcinoma substantially without the associated adverse effects of estrogen therapy, and thus serve as an effective and acceptable treatment for said diseases and conditions.

SUMMARY OF THE INVENTION

This invention provides novel 3-aroylbenzo[b]thiophenes having the formula

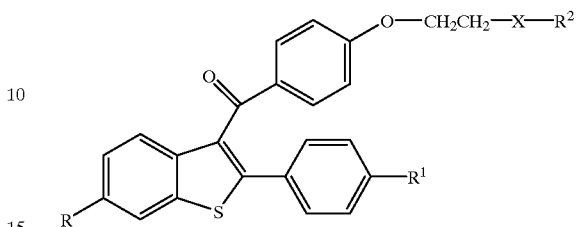

where
X is a bond or —CH$_2$—;
R$^2$ is a heterocyclic ring selected from pyrrolidino, piperidino or hexamethyleneimino;
R is OH —OSO$_2$—(CH$_2$)$_n$—CH$_3$ or

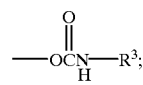

R$^1$ is hydrogen, OH, fluoro, chloro, —OSO$_2$—(CH$_2$)$_n$—CH$_3$, or

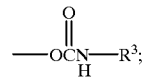

each R$^3$ is independently C$_1$–C$_6$ alkyl, C$_3$–C$_6$ cycloalkyl, unsubstituted or substituted phenyl where the substituent is fluoro, chloro, C$_1$–C$_3$ alkyl or C$_1$–C$_3$ alkoxy;
each n is independently 3, 4 or 5; and pharmaceutically acceptable salts and solvates thereof; provided that at least one of R and R$^1$ is —OSO$_2$—(CH$_2$)$_n$—CH$_3$ or

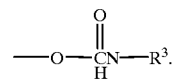

The present invention also provides pharmaceutical formulations comprising a compound of Formula I, in association with a pharmaceutically acceptable carrier, diluent or excipient.

The present invention also provides methods of preventing bone loss, treating hypercholesterolemia, and treating hormone dependent mammalian breast and uterine carcinoma comprising administering to a mammal in need of such treatment an effective amount of a compound according to formula I.

DETAILED DESCRIPTION OF THE INVENTION

The compounds of Formula I can be unambiguously named at least using methanone as the molecular skeleton or using benzo[b]thiophene as the molecular skeleton. For illustrative purposes, compounds of Formula I are named below using one or both molecular skeletons.

The general chemical terms used in the description of a compound of formula I have their usual meanings. For example, the term "alkyl" by itself or as part of another substituent means a straight or branched chain alkyl radical having the stated number of carbon atoms such as methyl, ethyl, propyl, and isopropyl and higher homologues and isomers where indicated.

The term "alkoxy" means an alkyl group having the stated number of carbon atoms linked by an oxygen atom, such as methoxy, ethoxy, propoxy, and also includes branched chain structures such as, for example, isopropoxy.

The benzo[b]thiophenes of Formula I inhibit the loss of bone that results from a lack of endogenous estrogen such as occurs in women following cessation of menstruation due to natural, surgical, or other processes. The reduction of bone density and mass that occurs in men is also tied to the loss of hormonal regulation and is therefore also a target for therapy according to methods of the present invention.

The benzo[b]thiophenes of Formula I should also lower serum cholesterol levels in humans. Excess serum cholesterol may result from a variety of conditions and disorders including a lack of endogenous estrogen such as occurs in women following cessation of menstruation due to natural, surgical, or other processes and patients having gonadal dysgenesis.

The compounds of formula (I), are also useful in therapeutically treating hormonally dependent mammalian breast and uterine carcinoma when administered in an effective amount. The term "therapeutically treating hormonally dependent breast and uterine carcinoma", as employed herein means adversely affecting the existence or growth including prophylactic measures, of breast and uterine carcinoma in mammals. The term "effective amount" means that dosage of active substance sufficient to provide prophylactic or therapeutic treatment of mammalian breast and uterine carcinoma.

The term "hormonally dependent carcinoma" is generally understood in the art to mean those carcinomas in which the growth thereof is influenced, in any manner, by the presence, absence, abundance or insufficiency of mammalian hormones. Such hormones include but are not limited to estrogen and prolactin.

The benzothiophenes of Formula I are a series of nonsteroidal compounds that exhibit high affinity for conventional estrogen receptors in primary sex target tissues. However, they elicit minimal estrogenic responses in those tissues, and actually serve as potent antagonists of natural estrogens such as estradiol. In contrast to other structurally distinct antiestrogen compounds, the benzothiophenes of Formula I are able to antagonize classical estrogenic responses in primary sex target tissues while eliciting an estrogenic response on bone density, and on serum cholesterol levels. This dichotomy indicates selective agonist/antagonist actions on specific target cells which are highly desirable in preventing bone loss and in treating hypercholesterolemia. Accordingly, a primary benefit of the current discovery is that the benzothiophenes of formula I inhibit bone loss, and lower serum cholesterol levels, but do not elicit significant estrogenic responses in the primary sex target tissues. Thus, the current invention provides methods of inhibiting bone loss, and lowering serum cholesterol levels, comprising administering to a human in need of treatment, an amount of a compound of formula I that inhibits bone loss and/or lowers serum cholesterol levels, but does not significantly affect the primary sex target tissues.

Preferred compounds of the present invention are those of formula I where $R^2$ is pyrrolidino or piperidino; R is —$OSO_2$—$(CH_2)_n$—$CH_3$; $R^1$ is selected from fluoro, chloro or —$OSO_2$—$(CH_2)_n$—$CH_3$; each n is independently 3, 4 or 5, and pharmaceutically acceptable acid addition salts and solvates.

Particularly preferred compounds are those of formula I where $R^2$ is a piperidino ring; R is —$OSO_2$—$(CH_2)_n$—$CH_3$; $R^1$ is —$OSO_2$—$(CH_2)_n$—$CH_3$; and each n is independently 3 or 4, and pharmaceutically acceptable acid addition salts and solvates thereof.

As mentioned above, the invention includes pharmaceutically acceptable salts of the compounds defined by the above Formula I. A compound of formula I can react with any of a number of nontoxic inorganic bases, and nontoxic inorganic and organic acids, to form a pharmaceutically acceptable salt. Acids commonly employed to form a pharmaceutically acceptable acid addition salt are inorganic acids such as hydrochloric acid, hydrobromic acid, hydroiodic sulfuric acid, phosphoric acid, and the like, and organic acids such as p-toluene-sulfonic, methanesulfonic acid, p-bromo-phenyl-sulfonic acid, carbonic acid, succinic acid, citric acid, benzoic acid, acetic acid, and the like. Examples of such pharmaceutical acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, malonate, succinate, suberate, sebacate, fumarate, maleate, butyne-1, 4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, anphthalene-1-sulfonate, naphthalene-2-sulfonate, mandelate, and the like. Preferred pharmaceutically acceptable acid addition salts are those formed with mineral acids such as hydrochloric acid and hydrobromic acid, and those formed with organic acids such as citric acid.

Base addition salts include those derived from nontoxic inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate. The potassium and sodium salt forms are particularly preferred.

The compounds of the present invention can be made according to established procedures, such as those detailed in U.S. Pat. No. 4,133,814 and U.S. Pat. No. 4,418,068, both of which are incorporated by reference herein. Examples of the preparation of analogous compounds are provided in the U.S. Patents discussed above. In general, the process starts with a benzo[b]thiophene having a 6-hydroxyl group and a 2-(4-hydroxyphenyl) group. The starting compound is protected, alkylated, and optionally deprotected to form the formula I compounds. Further formula I compounds may then be formed as desired. Specific preparations of compounds of the present invention are described below. Modifications to the above methods may be necessary to accommodate reactive functionalities of particular substituents. Such modifications would be both apparent to, and readily ascertained by, those skilled in the art.

The pharmaceutically acceptable acid addition salts are typically formed by reacting a compound of formula I with an equimolar or excess amount of base or acid. The reactants are generally combined in a mutual solvent such as diethyl ether or benzene. The salt normally precipitates out of solution within about one hour to 10 days and can be isolated by filtration or the solvent can be stripped off by conventional means.

In addition, some of the formula I compounds may form solvates with water or organic solvents such as ethanol. These solvates are also contemplated for use in the methods of this invention.

The following examples will illustrate preparation of the compounds of this invention but are not intended to limit it in any way.

EXAMPLE 1

Preparation of [6-(n-Butylsulfonoyl)-2-[4-(n-butylsulfonoyl)phenyl]benzo[b]thien-3-yl][4-[2-(1-piperidinyl)ethoxy]-phenyl]methanone 5.1 g (10 mmol) of [6-hydroxy-2-(4-hydroxyphenyl) benzo[b]thien-3-yl]-[4-[2-(1-piperidinyl)ethoxyphenyl] methanone, hydrochloride was suspended in 250 mL of dry THF and 7.1 g (70 mmol) of triethylamine was added. The reaction mixture as cooled to 0° C. in an ice bath and 10 mg of dimethylamino pyridine (DMAP) was added. 4.7 g (30 mmol) of n-butylsulfonoyl chloride was slowly added. The reaction mixture was placed under a nitrogen atmosphere and allowed to warm slowly to room temperature and continued for 72 hours. The reaction mixture was filtered and evaporated to an oil. The oily residue was dissolved in $CHCl_3$ and chromatographed on a silica gel column, eluted with a linear gradient of $CHCl_3$ to $CHCl_3$—MeOH (19:1; V:V). The desired fractions were combined and evaporated to dryness to afford 5.60 g of the title compound as a tan amorphous powder.

$C_{36}H_{43}NO_8S_3$

MS (FD) m/e=714 (M+1)

NMR was consistent with the proposed structure.

EXAMPLE 2

Preparation of [6-(n-Butylsulfonoyl)-2-[4-(n-butylsulfonoyl)phenyl]benzo[b]thien-3-yl][4-[2-(1-piperidinyl)ethoxy]-phenyl]methanone, Hydrochloride 5.4 g of [6-(n-Butylsulfonoyl)-2-[4-(n-butylsulfonoyl) phenyl]benzo[b]thien-3-yl][4-[2-(1-piperidinyl)ethoxy]-phenyl]methanone was dissolved in ethyl acetate (EtOAc) and a solution of ether, saturated with HCl, was added until no more precipitate was formed. The liquid was decanted off and the solid was triturated with ether. The title compound was crystallized from hot EtOAc to afford 3.74 g, as a white powder.

$C_{36}H_{43}NO_8S_3$—HCl

| Elemental Analysis: | C | H | N |
|---|---|---|---|
| Calculated: | 57.7 | 5.38 | 1.87 |
| Found: | 57.75 | 5.93 | 1.93 |

NMR was consistent with the proposed structure.

EXAMPLE 3

Preparation of [6-(n-Pentylsulfonoyl)-2-[4-(n-pentylsulfonoyl)phenyl]benzo[b]thien-3-yl][4-[2-(1-piperidinyl)ethoxy]-phenyl]methanone 3 g (5.9 mmol) of [6-hydroxy-2-(4-hydroxyphenyl)benzo [b]thien-3-yl]-[4-[2-(1-piperidinyl)ethoxy]phenyl] methanone, hydrochloride was suspended in 100 mL of THF and 10 mg of DMAP was added followed by 3 g (30 mmol) of triethylamine. The reaction mixture was stirred at room temperature and under a nitrogen blanket for about 20 minutes. 2.5 g (14.7 mmol) of n-pentyl sulfonoyl chloride was dissolved in 25 mL of THF and slowly added to the stirring reaction mixture. The reaction was allowed to proceed at room temperature and under nitrogen for eighteen hours. The reaction mixture was filtered and the volatiles were removed by evaporation in vacuo. The resulting material was dissolved in a small amount of $CHCl_3$ and chromatographed (HPLC) on a silica gel column eluted with a linear gradient starting with $CHCl_3$ and ending with $CHCl_3$—MeOH (19:1 v/v). The desired fractions were determined by Thin Layer Chromatography (TLC), combined and evaporated down to afford 3.82 g of the title compound as thick oil.

$C_{38}H_{47}NO_8S_3$

NMR: consistent with the proposed structure

MS: (FD) m/e=743 (M+2)

| Elemental Analysis: | C | H | N |
|---|---|---|---|
| Calculated: | 61.51 | 6.39 | 1.89 |
| Found: | 57.63 | 6.44 | 1.50 |

EXAMPLE 4

Preparation of [6-(n-Pentylsulfonoyl)-2-[4-(n-pentylsulfonoyl)phenyl]benzo[b]thien-3-yl][4-[2-(1-piperidinyl)ethoxy]-phenyl]methanone, Hydrochloride 3.7 g of [6-(n-Pentylsulfonoyl)-2-[4-(n-pentylsulfonoyl) phenyl]benzo[b]thien-3-yl][4-[2-(1-piperidinyl)ethoxy]-phenyl]methanone were dissolved in 25 mL of EtOAc and a solution of HCl—$Et_2O$ diethyl ether was added. A precipitate formed and the liquid decanted off. The gummy solid was triturated with $Et_2O$ and dried in vacuo at room temperature to afford 2.12 g of the title compound as a white amorphous and hygroscopic solid.

$C_{38}H_{47}NO_8S_3$ HCl

NMR: consistent with the proposed structure

| Elemental Analysis: | C | H | N |
|---|---|---|---|
| Calculated: | 58.63 | 6.22 | 1.80 |
| Found: | 57.35 | 6.45 | 1.38 |

EXAMPLE 5

Preparation of [6-(n-Hexylsulfonoyl)-2-[4-(n-hexysulfonoyl)phenyl]benzo[b]thien-3-yl][4-[2-(1-piperidinyl)ethoxy]-phenyl]methanone 3 g (5.9 mmol) of [6-hydroxy-2-(4-hydroxyphenyl)benzo [b]thien-3-yl][4-[2-(1-piperidinyl)ethoxy]phenyl] methanone hydrochloride was suspended in 250 mL of THF and 10 mg of DMAP was added. 4 g (40 mmol) of triethylamine was added and the reaction mixture was stirred for 20 minutes at room temperature under a nitrogen blanket. 3.6 g (19.6 mmol) of n-hexylsulfonoyl chloride in 25 mL of THF was slowly added to the reaction mixture. The reaction was allowed to proceed at room temperature and under nitrogen for 3 days. The reaction mixture was evaporated down in vacuo and resuspended in EtOAc and washed with water. The organic layer was dried by filtering it through anhydrous $Na_2SO_4$ and evaporated to a yellow oil. The oil was dissolved in $CHCl_3$ and chromatographed (HPLC) on a silica gel column and eluted with a linear gradient starting with $CHCl_3$ and ending with $CHCl_3$—MeOH (19:1 v/v). The desired fractions were determined by TLC, combined and evaporated down to afford 3.14 g of the title compound as a thick oil.

$C_{40}H_{51}NO_8S_3$

NMR: consistent with the proposed structure
MS: (FD) m/e=771 (M+1)

| Elemental Analysis: | C | H | N |
|---|---|---|---|
| Calculated: | 62.39 | 6.68 | 1.82 |
| Found: | 62.33 | 6.62 | 2.03 |

EXAMPLE 6

Preparation of [6-(n-Hexylsulfonoyl)-2-[4-(n-hexysulfonoyl)phenyl]benzo[b]thien-3-yl][4-[2-(1-piperidinyl)ethoxy]-phenyl]methanone, Hydrochloride 3 g of [6-(n-Hexylsulfonoyl)-2-[4-(n-hexysulfonoyl)phenyl]benzo[b]thien-3-yl][4-[2-(1-piperidinyl)ethoxy]-phenyl]methanone was dissolved in 20 mL of EtOAc and HCl—Et$_2$O was added. No precipitate formed. The reaction mixture was evaporated to a thick oil and was triturated several times with Et$_2$O and dried in vacuo at room temperature to afford 1.64 g of the title compound as a white amorphous and hygroscopic powder.

NMR: consistent with the proposed structure

| Elemental Analysis: | C | H | N |
|---|---|---|---|
| Calculated: | 59.67 | 6.50 | 1.74 |
| Found: | 59.47 | 6.59 | 1.77 |

$C_{40}H_{51}NO_8S_3$—HCl

EXAMPLE 7

Preparation of [6-(n-Butylsulfonoyl)-2-[4-(n-butylsulfonoyl)phenyl]benzo[b]thien-3-yl][4-[2-(1-piperidinyl)ethoxy]-phenyl]methanone, Citrate 2 g (2.8 mmol) of [6-(n-Butylsulfonoyl)-2-[4-(n-butylsulfonoyl)phenyl]benzo[b]thien-3-yl][4-[2-(1-piperidinyl)ethoxy]-phenyl]methanone was dissolved in 200 mL of acetone and 0.63 g (3 mmol) of citric acid was added. The reaction mixture remained at room temperature and under a nitrogen blanket for eighteen hours. The reaction mixture was evaporated in vacuo at 50° C. The reaction mixture was triturated several times with ether and dried at room temperature in vacuo to afford 2.35 g of the title compound as a white amorphous and hygroscopic powder.

| Elemental Analysis: | C | H | N |
|---|---|---|---|
| Calculated: | 55.68 | 5.67 | 1.55 |
| Found: | 55.39 | 5.60 | 1.60 |

NMR: consistent with the proposed structure

EXAMPLE 8

Preparation of [6(n-butylsulfonoyl)-2-[4-(n-butylsulfonoyl)phenyl]benzo[b]thien-3-yl][4-[3-(1-piperidinyl)propyloxy]-phenyl]methanone 2.5 g (4.77 mmol) of [6-hydroxy-2-[4-hydroxyphenyl]benzo[b]thien-3-yl][4-[3-(1-piperidinyl)propyloxy]phenyl]methanone hydrochloride was dissolved in 100 mL of THF, 3.9 g (39 mmol) of triethylamine and 10 mg of DMAP were added. The reaction mixture was stirred for 15 minutes at room temperature and under a nitrogen blanket. 4 g (25.5 mmol) of n-butylsulfonoyl chloride in 15 mL of THF was slowly added. The reaction was allowed to proceed for eighteen hours at room temperature and under nitrogen. The reaction was quenched with the addition of 25 mL MeOH and volume reduced in vacuo. The crude product was chromatographed on a silica gel column, eluted with CHCl$_3$—MeOH (19:1 v/v). The desired fractions were determined by TLC, combined, and evaporated to a tan oil.

EXAMPLE 9

Preparation of [6-(n-butylsulfonoyl)-2-[4-(n-butylsulfonoyl)phenyl]benzo[b]thien-3-yl][4-[3-(1-piperidinyl)propyloxy]-phenyl]methanone, hydrochloride

[6-(n-butylsulfonyl)-2-[4-(n-butylsulfonoyl)phenyl]benzo[b]thien-3-yl][4-[3-(1-piperidinyl)propyloxy]-phenyl]methanone was dissolved in EtOAC-hexane and HCl gas was bubbled in. The reaction mixture was evaporated down and chromatographed (HPLC) on a silica gel column eluted with CHCl$_3$ and then with CHCl$_3$—MeOH (19:1 v/v). The desired fractions were determined by TLC and combined and evaporated down to a tan amorphous powder to afford 2.5 g of the title compound.

NMR: consistent with the proposed structure
MS: (FD) m/e=723 (M—HCl)

| Elemental Analysis: | C | H | N |
|---|---|---|---|
| Calculated: | 58.14 | 6.07 | 1.83 |
| Found: | 57.90 | 6.05 | 1.82 |

$C_{37}H_{46}NO_8S_3$—HCl

EXAMPLE 10

Preparation of [6-(n-Butylsulfonoyl)-2-[4-Butylsulfonoyl)phenyl]benzo[b]thien-3-yl][4-[2-(1-pyrrolidinyl)ethoxy]phenyl]methanone 1.5 g of [6-hydroxy-2-[4-hydroxyphenyl]benzo[b]thien-3-yl][4-[2-(1-pyrrolidinyl)ethoxy]-phenyl]methanone hydrochloride (3 mmol) was suspended in 200 mL of THF. 1.5 g of triethylamine (15 mmol) and 10 mg of 4-N,N-dimethylaminopyridine were added. The reaction mixture was stirred for several minutes under a nitrogen atmosphere. 1.56 g of n-butylsulfonoyl chloride (10 mmol) was dissolved in 50 mL of THF and slowly added to the reaction mixture over a twenty minute period. The reaction mixture was stirred for eighteen hours at room temperature and under a nitrogen atmosphere. The reaction mixture was evaporated to a gum in vacuo. The crude product was suspended in 100 mL of EtOAc and washed with NaHCO$_3$ solution and subsequently with water. The organic layer was dried by filteration through anhydrous Na$_2$SO$_4$ and evaporated to a yellow oil. The final product was crystallized from hot EtOAc-hexane to afford 410 mg of the title compound.

NMR was consistent with the proposed structure
MS: m/e=700 (M+1) FD

| Elemental Analysis: | C | H | N |
|---|---|---|---|
| Calculated: | 60.2 | 5.86 | 2.01 |
| Found: | 59.94 | 5.94 | 2.00 |

MW=699
C$_{35}$H$_{41}$NO$_8$S

EXAMPLE 11

Preparation of [6-(n-butylsulfonoyl)-2-[4-(n-butylsulfonoyl)-phenyl]benzo[b]thien-3-yl]-[4-[2-(1-pyrrolidinyl)ethoxy]-phenyl]methanone hydrochloride 350 mg of [6-(n-Butylsulfonoyl)-2-[4-Butylsulfonoyl) phenyl]benzo[b]thien-3-yl]-[4-[2-(1-pyrrolidinyl)ethoxy] phenyl]methanone (0.5 mmol) was dissolved in 10 mL of EtOAc and a saturated solution of HCl in ether was added. No precipitate formed and the reaction mixture was evaporated to a gummy, white solid. The product was triturated with Et$_2$O (2x) and filtered and dried in vacuo at room temperature to afford 220 mg of the title compound.

NMR: consistent with the proposed structure

| Elemental Analysis: | C | H | N |
|---|---|---|---|
| Calculated: | 57.09 | 5.75 | 1.90; |
| Found: | 57.27 | 5.91 | 1.86 |

MW=736.37
C$_{35}$H$_{41}$NO$_8$S$_3$—HCl

EXAMPLE 12

Preparation of [6-hydroxy-2-[4-(n-butylsulfonoyl) phenyl]benzo[b]-thien-3-yl]-[4-[2-(1-piperidinyl) ethoxy]phenyl]methanone 20 g of [6-hydroxy-2-[4-hydroxyphenyl]benzo[b]thien-3-yl]-[4-[2-(1-piperidinyl)ethoxy]phenyl]methanone (Raloxifene) hydrochloride (0.04 mol) was suspended in 250 mL of THF. 10 g of triethylamine (0.1 mol) and 10 mg of 4-N,N-dimethylaminopyridine were added. The reaction mixture was stirred for several minutes under nitrogen. 6.25 g of n-butylsulfonoylchloride (0.04 mol) was dissolved in 25 ml of THF and slowly added to the reaction mixture over a period of twenty minutes. The reaction was allowed to continue for 5 days at room temperature and under N$_2$. The reaction mixture was evaporated to a gum and suspended in EtOAc. The EtOAc mixture was washed successively with water, dilute NaHCO$_3$, and water. The EtOAc solution was dried by filteration through anhydrous Na$_2$SO$_4$ and evaporated to an amorphous solid.

The resulting solid was dissolved in 50 mL of CH$_2$Cl$_2$ and chromatographed (HPLC) on a silica gel column eluted with a linear gradient of CHCL$_3$ to CHCL$_3$—MeOH (19:1)(v/v). Four fractions were determined by TLC and evaporated in vacuo to amorphous solids:

Fraction A: [6-(n-Butylsulfonoyl)-2-[4-(n-butylsulfonoyl)phenyl]benzo[b]thien-3-yl][4-[2-(1-piperidinyl)ethoxy]-phenyl]methanone, 5.43 g Fraction B: [6-hydroxy-2-[4-(n-butylsulfonoyl)phenyl] benzo[b]-thien-3-yl]-[4-[2-(1-piperidinyl)ethoxy] phenyl]methanone, 2.19 g, Rf=0.50, silica gel, CHCl$_3$—MeOH (19:1)v/v Fraction C: [6-n-butylsulfonyl-2-(4-hydroxyphenyl) benzo[b]thien-3-yl]-[4-[2-(1-piperidinyl)ethoxy] phenyl]methanone, 3.60 g Rf=0.41, silica gel, CHCl$_3$—MeOH (19:1)v/v Fraction D: Raloxifene, 3.94 g All of Fraction B was dissolved in hot EtOAc and hexane was added and the title compound crystallized out to afford 1.89 g of the title compound.

NMR: consistent with proposed structure
MS: m/e=594(M+1) FD

| Elemental Analysis: | C | H | N |
|---|---|---|---|
| Calculated: | 64.5 | 5.90 | 2.36 |
| Found: | 64.85 | 6.07 | 2.49 |

C$_{32}$H$_{35}$NO$_6$S$_2$

EXAMPLE 13

Preparation of [6-hydroxy-2-[4-(n-butylsulfonoyl) phenyl]benzo[b]thien-3-yl]-[4-[2-(1-piperidinyl) ethoxy]phenyl]methanone hydrochloride 1.7 g of [6-hydroxy-2-[4-(n-butylsulfonoyl)phenyl]benzo [b]-thien-3-yl]-[4-[2-(1-piperidinyl)ethoxy]phenyl] methanone (2.86 mmol) was dissolved in EtOAc and a saturated solution of HCl—Et$_2$O was added. A thick white precipitate formed. The liquid was decanted off. The remaining solid was triturated with Et$_2$O (2x) and dried to afford 1.57 g of the title compound as a white amorphous powder.

NMR: consistent with the proposed structure.

| Elemental Analysis: | C | H | N |
|---|---|---|---|
| Calculated: | 60.99 | 5.76 | 2.22; |
| Found: | 61.17 | 5.88 | 2.27 |

MW=630.23
C$_{32}$H$_{35}$NO$_6$S$_2$—HCl
MS: m/e=594 (M—HCl) F.D.

EXAMPLE 14

Preparation of [6-n-butylsulfonoyl-2-[4-hydroxyphenyl]benzo[b]thien-3-yl]-[4-(2-(1-piperidinyl)ethoxy]phenyl]methanone All of fraction C from Example 17 was dissolved in 50 mL of hot EtOAc and hexane. No crystallization occurred The solvents were evaporated in vacuo to afford 3.17 g of the title compound as oily, white solid.

NMR: consistent with the proposed structure.
MS: m/e=594 (M+1) FD

| Elemental Analysis: | C | H | N |
|---|---|---|---|
| Calculated: | 64.5 | 5.90 | 2.36; |
| Found: | 64.37 | 5.87 | 2.28 |

MW=593
C$_{32}$H$_{35}$NO$_6$S

EXAMPLE 15

Preparation of [6-n-butylsulfonoyl-2-[4-hydroxyphenyl]benzo[b]thien-3-yl]-[4-[2-(1-piperidinyl)ethoxy]phenyl]methanone hydrochloride 3 g of [6-n-butylsulfonoyl-2-[4-hydroxyphenyl]benzo[b] thien-3-yl]-[4-[2-(1-piperidinyl)ethoxy]phenyl]methanone was dissolved in 50 mL of EtOAc and a solution of Et$_2$O saturated with HCl was added. A thick white precipitate formed and the liquid was decanted off. The solid was triturated (2x) with Et$_2$O and dried. This afforded 2.51 g of the title compound as a white amorphous powder.

NMR: consistent with the proposed structure.

| Elemental Analysis: | C | H | N |
|---|---|---|---|
| Calculated: | 60.99 | 5.76 | 2.22; |
| Found: | 60.71 | 5.84 | 2.21 |

MW=630.23

$C_{32}H_{35}NO_6S_2$—HCl

MS: m/e=594 (M—HCl) F.D.

EXAMPLE 16

Preparation of [6-[N-(4-Chlorophenyl)carbamoyl]-2-[4-[N-(4-chlorophenyl)carbamoyl]phenyl]benzo[b]thien-3-yl][4-[2-(1-piperidinyl)ethoxy]-phenyl]methanone 5.56 g (10.7 mmol) of [6-hydroxy-2-(4-hydroxyphenyl)benzo[b]thien-3-yl]-[4-[2-(1-piperidinyl)ethoxy]phenyl]methanone was dissolved in 200 mL of dry THF and 5.45 g (35.2 mmol) of 4-chlorophenyl isocynate was added. The reaction mixture was stirred at room temperature under an atmosphere of nitrogen. After 18 hours, the solvent was removed by evaporation in vacuo, and redissolved in $CHCl_3$. The $CHCl_3$ solution was cooled to −20° C. for 24 hours and the precipitate formed was filtered off. The remaining solution was chromatographed (Waters Prep 500, HPLC) on a silica gel column, eluted with a linear gradient of $CHCl_3$ ending with $CHCl_3$—MeOH (19:1)(v/v). The desired fractions were determined by TLC, combined and evaporated to dryness to afford 4.01 g of the title compound as a tan amorphous powder.

$C_{42}C_{35}Cl_2N_3O_6S$

| Elemental Analysis: | C | H | N |
|---|---|---|---|
| Calculated: | 64.6 | 4.48 | 5.38 |
| Found: | 65.69 | 4.51 | 4.53 |

MS (FD) m/e=779,781

EXAMPLE 17

Preparation of [6-[N-(4-Chlorophenyl)carbamoyl]-2-[4-[N-(4-chlorophenyl)carbamoyl]phenyl]benzo[b]thien-3-yl][4-[2-(1-piperidinyl)ethoxy]-phenyl]methanone Hydrochloride 4.01 g of [6-[N-(4-Chlorophenyl)carbamoyl]-2-[4-[N-(4-chlorophenyl)carbamoyl]phenyl]benzo[b]thien-3-yl][4-[2-(1-piperidinyl)ethoxy]-phenyl]methanone was dissolved in 200 mL of ether and a small amount of THF added to affect solution. A solution of ether, which had been saturated with HCl, was added until no further precipitate formed. The reaction mixture was evaporated to dryness and triturated with ether several times. An attempt was made to crystalize the salt from hot EtOAc and absolute EtOH, which did work. Evaporation of the solvent, afforded 2.58 g of the title compound as a tan amorphous powder.

$C_{42}H_{35}Cl_2N_3O_6S$—HCl

| Elemental Analysis: | C | H | N |
|---|---|---|---|
| Calculated: | 61.73 | 4.44 | 5.14 |
| Found: | 57.43 | 4.29 | 4.19 |

NMR: Consistent with the proposed structure and contains an indeterminate amount of solvent.

EXAMPLE 18

Preparation of [6-(N-n-butylcarbamoyl]-2-[4-(N-n-butylcarbamoyl)phenyl]benzo[b]thien-3-yl][4-[2-(1-piperidinyl)ethoxy]-phenyl]methanone 4.47 g (9 mmol) of [6-hydroxy-2-(4-hydroxyphenyl)benzo[b]thien-3-yl][4-[2-(1-piperidinyl)ethoxy]phenyl]methanone was dissolved in 250 mL of THF and 4 g (40 mmol) of n-butylisocyanate was added. The reaction mixture, at room temperature and under nitrogen, was allowed to react for 72 hours. The reaction mixture had evaporated by the end of this time and the residue was dissolved in a minimal amount of $CHCl_3$. This solution was chromatographed (HPLC) on a silica gel column, eluted with a linear gradient of $CHCl_3$ to $CHCl_3$—MeOH (19:1) to afford 4.87 g of the title compound as a tan amorphous powder.

| Elemental Analysis: | C | H | N |
|---|---|---|---|
| Calculated: | 67.73 | 6.75 | 6.52 |
| Found: | 66.43 | 6.67 | 6.24 |

MS (FD) m/e=672 (M+1)

NMR was consistent with the proposed structure.

EXAMPLE 19

Preparation of [6-(N-Methylcarbamoyl)-2-[4-(N-methylcarbamoyl)-phenyl]benzo[b]thien-3-yl][4-[2-(1-piperidinyl)ethoxy]phenyl]methanone A suspension of 3 g (5.9 mmol) of [6-hydroxy-2(4-hydroxyphenyl)]benzo[b]thien-3-yl][4-[2-(1-piperidinyl)ethoxy]phenyl]methanone hydrochloride in 250 mL of anhydrous THF was prepared. To this suspension was added 2 g (10 mmol) of triethylamine and the reaction mixture was stirred at room temperature for approximately 15 minutes under a nitrogen atmosphere. To the stirring mixture was added 5.8 g (20 mmol) of methylisocyanate. The reaction was allowed to continue for 36 hours. The reaction mixture was filtered and evaporated to dryness in vacuo. The residue was dissolved in 30 mL of chloroform and chromatographed (HPLC) on a silica gel column, eluted with a linear gradient of solvent of chloroform to chloroform-methanol (19:1). The fractions were analyzed by TLC and the desired fractions were combined and evaporated to dryness in vacuo to afford 2.2 g of the title compound as an amorphous powder.

NMR: Consistent with the proposed structure.
IR: 3465, 2942, 1741 cm-1 ($CHCl_3$)
MS: m/e=588 (M+1) FD
$C_{32}H_{33}N_3O_6S$.

EXAMPLE 20

Preparation of [6-(N-Methylcarbamoyl)-2[4-(N-methylcarbamoyl)-phenyl]benzo[b]thien-3-yl][4-[2-(1-piperidinyl)ethoxy]phenyl]methanone Hydrochloride 2 g of the compound of [6-(N-Methylcarbamoyl)-2[4-(N-methylcarbamoyl)-phenyl]benzo[b]thien-3-yl][4-[2-(1- piperidinyl)ethoxy]phenyl]methanone was dissolved in 20 mL of EtOAc and a solution HCL-ether was added, forming a white precipitate. The reaction mixture was evaporated to dryness in vacuo. The solids were crystallized from acetone-EtOAc, filtered and washed with EtOAc and dried to afford 1.98 g of the title compound.

NMR: Consistent with the proposed structure.

| Elemental Analysis: | C | H | N |
|---|---|---|---|
| Calculated: | 61.58 | 5.49 | 6.78 |
| Found: | 61.25 | 5.96 | 5.97. |

$C_{32}H_{34}ClN_3O_6S$.

EXAMPLE 21

Preparation of [6-(N-Ethylcarbamoyl)-2[4-(N-ethylcarbamoyl)phenyl]benzo[b]thien-3-yl][4-[2-(1-piperidinyl)ethoxy]phenyl]methanone 4 g (7.85 mmol) of [6-hydroxy-2-(4-hydroxyphenyl)benzo[b]thien-3-yl][4-[2-(1-piperidinyl)ethoxy]phenyl]methanone hydrochloride was suspended in 250 mL of anhydrous THF and 3 g (30 mmol) of triethylamine was added. The reaction mixture was stirred at room temperature under nitrogen for 15 minutes. 1.67 g (23.5 mmol) of ethylisocyanate was added. After 24 hours, the reaction was checked by TLC, and was not complete. An additional 4.5 g of the isocyanate was added. After 96 hours, the reaction mixture was filtered and chromatographed as in Example 19 to afford 4.23 g of the title compound as a white amorphous powder.

NMR: Consistent with the proposed structure.
MS: m/e=616 (M+1) FD
$C_{34}H_{37}N_3O_6S$.

EXAMPLE 22

Preparation of [6-(N-ethylcarbamoyl)-2-[4-(N-ethylcarbamoyl)phenyl]benzo[b]thien-3-yl][4-[2-(1-piperidinyl)ethoxy]phenyl]methanone hydrochloride This compound was prepared by substantially the same procedures of Example 20, to afford 3.58 g of the title compound.

NMR: Consistent with the proposed structure.

| Elemental Analysis: | C | H | N |
|---|---|---|---|
| Calculated: | 62.61 | 5.87 | 6.44; |
| Found: | 62.33 | 6.16 | 6.41. |

$C_{34}H_{38}ClN_3O_6S$.

EXAMPLE 23

Preparation of [6-(N-isoPropylcarbamoyl)-2[4-(N-isopropylcarbamoyl)phenyl]benzo[b]thien-3-yl][4-[2-(1-piperidinyl)ethoxy]phenyl]methanone 4 g (7.85 mmol) of [6-hydroxy-2-(4-hydroxyphenyl)benzo[b]thien-3-yl][4-[2-(1-piperidinyl)ethoxy]phenyl]methanone hydrochloride was suspended in 250 mL of anhydrous THF and 3 g (30 mmol) of triethylamine was added. The reaction mixture was stirred for 15 minutes at room temperature and under nitrogen.

2.77 g (32.6 mmol) of isopropylisocyanate was added. After 24 hours, the reaction was checked by TLC for completeness and was not complete. An additional 10.8 g (130.4 mmol) of the isocyanate was added and the reaction was allow to continue for another 96 hours. The desired compound was isolated substantially according to the procedures described in Example 19 to afford 4.01 g of the title compound as a tan amorphous powder.

NMR: Consistent with the proposed structure.
MS: m/e=644 (M+1) FD
$C_{36}H_{41}N_3O_6S$.

EXAMPLE 24

Preparation of [6-(N-isopropylcarbamoyl)-2-[4-(N-isopropylcarbamoyl)phenyl]benzo[b]thien-3-yl]-[4-[2-(1-piperidinyl)ethoxy]phenyl]methanone hydrochloride This compound was prepared by substantially following the procedures of Example 20 to afford 3.58 g of the title compound as a white crystalline powder.

NMR: Consistent with the proposed structure.

| Elemental Analysis: | C | H | N |
|---|---|---|---|
| Calculated: | 63.56 | 6.22 | 6.18 |
| Found: | 63.63 | 6.52 | 5.95 |

$C_{36}H_{42}ClN_3O_6S$.

EXAMPLE 25

Preparation of [6-(N-Cyclohexylcarbamoyl)-2[4-(N-cyclohexylcarbamoyl)phenyl]benzo[b]thienyl-3-yl][4-[2-(1-piperidinyl)ethoxy]phenyl]methanone 3 g (5.9 mmol) of [6-hydroxy-2-(4-hydroxyphenyl)benzo[b]thien-3-yl][4-[2-(1-piperidinyl)ethoxy]phenyl]methanone hydrochloride was suspended in 250 mL of anhydrous THF and 2 g (20 mmol)of triethylamine was added. The reaction mixture was stirred for 15 minutes at room temperature under nitrogen. 14.5 g (105 mmol) of cyclohexylisocyanate was added. The reaction was allowed to continue for 48 hours, then an additional 20 mmol of the isocyanate was added. After a further 24 hours, the desired product was isolated substantially according to the procedures of Example 19 to afford 4.07 g of the title compound as a tan amorphous powder.

NMR: Consistent with the proposed structure.
MS: m/e=724 (M+1) FD
$C_{42}H_{49}N_3O_6S$.

EXAMPLE 26

Preparation of 6-(N-Cyclohexylcarbamoyl)-2[4-(N-cyclohexylcarbamoyl)phenyl]benzo[b]thienyl-3-yl][4-[2-(1-piperidinyl)ethoxy]phenyl]methanone Hydrochloride 3.9 g of 6-(N-Cyclohexylcarbamoyl)-2[4-(N-cyclohexylcarbamoyl)phenyl]benzo[b]thienyl-3-yl][4-[2-(1-piperidinyl)ethoxy]phenyl]methanone was converted to its hydrochloride salt by substantially the same procedures as described for Example 20 and crystallized from hot EtOAc. This afforded 3 g of the title compound as a white powder.

NMR: Consistent with the proposed structure.

| Elemental Analysis: | C | H | N |
|---|---|---|---|
| Calculated: | 66.34 | 6.63 | 5.53 |
| Found: | 66.32 | 6.92 | 5.62 |

$C_{42}H_{50}ClN_3O_6S$.

EXAMPLE 27

Preparation of [6-(N-Phenylcarbamoyl)-2[4-(N-phenylcarbamoyl)phenyl]benzo[b]thien-3-yl][4-[2-(1-piperidinyl)ethoxy]phenyl]methanone 3 g (5.9 mmol) of [6-hydroxy-2[4-hydroxyphenyl)benzo[b]thien-3-yl][4-[2-(1-piperidinyl)ethoxy]phenyl]methanone hydrochloride was suspended in 250 mL of anhydrous THF and 2 g (20 mmol) of triethylamine was added. The reaction mixture was stirred for 15 minutes at room temperature under nitrogen. 5 mL of phenylisocyanate was added and the reaction was allow to continue for 96 hours. An additional 5 mL of isocyanate was added. After a further 48 hours, the reaction mixture was filtered and evaporated to an oil, The oil was triturated with heptane and the liquid decanted off. The oil was dissolved in chloroform and chromatographed (HPLC) on a silica gel column, eluted with a linear gradient of chloroform to chloroform-MeOH (19:1). The desired fractions were combined and evaporated to an oil to afford 3.31 g of the title compound.

NMR: Consistent with the proposed structure.

MS: m/e=711 and some 212 (diphenylurea)

$C_{42}H_{37}N_3O_6S$.

EXAMPLE 28

Preparation of [6-(N-Phenylcarbamoyl)-2[4-(N-phenylcarbamoyl)phenyl]benzo[b]thien-3-yl][4-[2-(1-piperidinyl)ethoxy]phenyl]methanone Hydrochloride 3.2 g of [6-(N-Phenylcarbamoyl)-2[4-(N-phenylcarbamoyl)phenyl]benzo[b]thien-3-yl][4-[2-(1-piperidinyl)ethoxy]phenyl]methanone was dissolved in EtOAc and filtered. HCl-ether was added to the solution and a white precipitate formed. The liquid was decanted off. The solid was dissolved in a small amount of acetone and filtered, then it is was evaporated to dryness to afford 270 mg of the title compound as a tan amorphous powder.

| Elemental Analysis: | C | H | N |
|---|---|---|---|
| Calculated: | 67.42 | 5.12 | 5.62 |
| Found: | 67.51 | 5.37 | 5.50 |

$C_{42}H_{38}ClN_3O_6S$.

By substantially following the procedures described above one skilled in the art can prepare the compounds of Formula I.

As noted above, the compounds of the present invention are useful for inhibiting bone loss, lowering serum cholesterol levels and treating hormone dependent mammalian breast and uterine carcinoma. Therefore, further embodiments of the present invention are methods for inhibiting bone loss, lowering serum cholesterol and treating hormone dependent breast and uterine carcinoma by administering to a mammal in need of treatment a bone loss inhibiting, serum cholesterol lowering or hormone dependent breast or uterine carcinoma inhibiting dose (effective amount) of a compound according to Formula I or a pharmaceutically acceptable salt or solvate thereof.

The term "effective amount" as used herein, means an amount of a compound of the present invention which is capable of inhibiting bone loss, lowering serum cholesterol levels or inhibiting hormone dependent breast and uterine carcinoma. The present methods include medical therapeutic and/or prophylactic treatment, as appropriate. The specific dose of compound administered according to this invention to obtain therapeutic and/or prophylactic effects will, of course, be determined by the particular circumstances surrounding the case, including, for example, the compound administered, the route of administration, and the condition being treated. A typical daily dose will contain a nontoxic dosage level of from about 0.1 mg/kg to about 1000 mg/kg of body weight of the active compound of this invention administered alone or administered with estrogen or in combination with estrogen. Preferred daily doses generally will be from about 0.5 to about 600 mg/kg and ideally from about 1.0 to about 300 mg/kg. Generally, accepted and effective daily doses of estrogen will be from about 0.01 to about 4.0 mg, and more typically from about 0.1 to about 2.0 mg.

The methods of the present invention are useful in men, as well as women. The substantial absence of estrogenic response should allow men to employ the method of the present invention without evidencing the feminizing response of estrogen or estrogen agonists such as gynecomastia. Preferably, however, the method of the present invention is useful in women, more particularly estrogen deficient women. The bone loss contemplated is a decrease in bone mass with a static bone volume such as osteoporosis and Cushing's disease. The estrogen deficiency could occur naturally, such as post-menopausal, or surgically. Patients undergoing or having undergone long-term administration of corticosteroids and those having gonadal dysgenesis may also employ the compounds, formulations and methods of the present invention.

The compounds can be administered by a variety of routes including oral, rectal, transdermal, subcutaneous, intravenous, intramuscular and intranasal. The compounds of the present invention are preferably formulated prior to administration. Therefore, another embodiment of the present invention is a pharmaceutical formulation comprising an effective amount of a compound of Formula I or a pharmaceutically acceptable salt or solvate thereof, alone or in combination with estrogen, and a pharmaceutically acceptable carrier, diluent or excipient therefor.

The active ingredient in such formulations comprises from 0.1% to 99.9% by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like. Typical formulations designed for topical administration are ointments, creams, gels, and lotions containing, for example, up to 10% by weight of the active compound.

The following formulation examples are illustrative only and are not intended to limit the scope of the invention in any way. "Active ingredient," of course, means a compound according to Formula I or a pharmaceutically acceptable salt or solvate thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
| --- | --- |
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| Active ingredient | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| Active ingredient | 50 mg |
| --- | --- |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| Isotonic saline | 1,000 ml |

The solution of the above ingredients generally is administered intravenously to a subject at a rate of 1 ml per minute.

The following evaluations were carried out in a model of post-menopausal osteoporosis where the effects of different treatments upon distal femur density and serum cholesterol were determined.

Bone Density

Seventy-five day old female Sprague Dawley rats (weight range of 225 to 275 g) were obtained from Charles River Laboratories (Portage, Mich.). They were housed in groups of 3 and had ad libitum access to food (calcium content approximately 1%) and water. Room temperature was maintained at 22.2°±1.7° C. with a minimum relative humidity of 40%. The photoperiod in the room was 12 hours light and 12 hours dark.

One week after arrival, the rats underwent bilateral ovariectomy under anesthesia (44 mg/kg Ketamine and 5 mg/kg Xylazine (Butler, Indianapolis, Ind.) administered intramuscularly). Treatment with vehicle, estrogen, or a compound of formula I was initiated on the day of surgery following recovery from anesthesia. Oral dosage was by gavage in 0.5 mL of 1% carboxymethylcellulose (CMC). Body weight was determined at the time of surgery and weekly thereafter and the dosage was adjusted with changes in body weight. Vehicle or estrogen treated ovariectomized (OVX) rats and non-ovariectomized (intact) rats were evaluated in parallel with each experimental group to serve as negative and positive controls.

The rats were treated daily for 35 days (6 rats per treatment group) and sacrificed by carbon dioxide asphyxiation on the 36th day. In some cases, cardiac blood samples (for cholesterol analysis) was collected from anesthetized (ketamine/xylazine) rats prior to carbon dioxide asphyxiation. The 35 day time period was sufficient to allow maximal reduction in bone density, measured as described herein. At the time of sacrifice, the uteri were removed, dissected free of extraneous tissue, and the fluid contents were expelled before determination of wet weight in order to confirm estrogen deficiency associated with complete ovariectomy. Uterine weight was routinely reduced about 75% in response to ovariectomy. The uteri were then placed in 10% neutral buffered formalin to allow for subsequent histological analysis.

The right femurs were excised and scanned at the distal metaphysis 1 mm from the patellar groove with single photon absorptiometry. Results of the densitometer measurements represent a calculation of bone density as a function of the bone mineral content and bone width.

Serum Cholesterol (4-day Assay)

Seventy-five day old female Sprague Dawley rats (weight range of 200 to 225 g) were obtained from Charles River Laboratories (Portage, Mich.). The animals were either bilaterally ovariectomized (OVX) or exposed to a Sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.7° C. with a minimum relative humidity of 40%. The photoperiod in the room was 12 hours light and 12 hours dark.

Dosing Regimen/Tissue Collection

After a one week acclimation period (therefore, two weeks post-OVX) daily dosing with test compound was initiated. All compounds were administered orally at 1 ml/kg body weight, unless otherwise stated. 17β-Estradiol was administered subcutaneously in a 20% polyethylene glycol vehicle, 17α-ethynyl estradiol and the test compound were given orally unless otherwise stated as a suspension in 1% carboxymethylcellulose or 20% cyclodextrin. Animals were dosed daily for 4 days. Following the 4-day dosing regimen animals were weighed and anesthetized with a ketamine: Xylazine (2:1, (V:V) mixture and a blood sample was collected by cardiac puncture. The animals were then sacrificed by asphyxiation with $CO_2$ and the uterus was removed through a midline incision and a wet weight was determined.

Cholestrol Analysis

Blood samples were allowed to clot at room temperature for 2 hrs, and serum was obtained following centrifugation for 10 min at 3000 rpm. Serum cholesterol was determined using a Boehringer Mannheim Diagnostics high performance cholesterol assay. Briefly, the cholesterol was oxidized to cholest-4-en-3-one and hydrogen peroxide. The hydrogen peroxide was then reacted with phenol and 4-aminophenazone in the presence of peroxidase to produce a p-quinonoe imine dye, which was read spectrophotometrically at 500 nm. Cholesterol concentration was then calculated against a standard curve. The entire assay was automated using a Biomek Automated Workstation.

Uterine Eosinophil Peroxidase Assay

Uteri from both bone density and serum cholesterol evaluations were kept at 4° C. until time of enzymatic analysis. The uteri were then homogenized in 50 volumes of 50 nM Tris buffer (pH—8.0) containing 0.005% Triton X-100. Upon addition of 0.01% hydrogen peroxide and 10 mM o-phenylenediamine (final concentrations) in Tris buffer, increase in absorbance was monitored for one minute at 450 nm. The presence of eosinophils in the uterus is an indication of estrogenic activity of a compound. The maximal velocity of a 15 second interval was determined over the initial, linear portion of the reaction curve.

Sources of Compounds

17β-estradiol, and 17α-ethynyl estradiol were obtained from Sigma Chemical Co., St. Louis, Mo.

Statistics

All experimental groups were comprised of five or six animals. Statistical comparisons were made using one way analysis of variance, and when statistical significance was indicated ($p \leq 0.05$), means were separated by post-hoc range analysis. Results are reported as percentage (%) change calculated in comparison to vehicle treated OVX controls.

In U.S. Pat. No. 4,418,068, the preparation of [6-(methylsulfonoyloxy)-2-[4-(methylsulfonoyloxy)phenyl]benzo[b]thien-3-yl][4-[2-(1-piperidinyl)ethoxy]phenyl]methanone hydrochloride; and [6-(phenylsulfonoyloxy)-2-[4-(phenylsulfonoyloxy)phenyl]benzo[b]thien-3-yl][4-[2-(1-piperidinyl)ethoxy]phenyl]methanone hydrochloride are disclosed as hydroxy-protected intermediates useful in the synthesis of the desired compounds disclosed in said patent. These intermediates were also prepared and evaluated in the test systems described above.

The results of the 4-day evaluations are set forth in Table 1 and the 35-day evaluations in Table 2. Tables 3 and 4 set forth results obtained on the protected intermediates from U.S. Pat. No. 4,418,068 using the same evaluation procedures and on sulfonate analogs outside the scope of the present invention where, according to Formula I, R and $R^1$ are —$OSO_2$—$(CH_2)_n$—$CH_3$ and n is 2 or 6; X is a bond; and $R^2$ is piperidino (4-day evaluation only).

TABLE 1

4-Day OVX

| Example No. | Dose (mg/kg) | Uterine Weight (% increase) | Eosinophil peroxidose (Vmax) | Serum Cholesterol (% decrease) |
|---|---|---|---|---|
| 1 | 0.1 | −7.2 | 5.2 | 32.0 |
|   | 1 | −8.9 | 5.6 | 44.8 |
|   | 10 | −6.4 | 5.0 | 65.2 |
| 2 | 0.01 | 0 | 4.2 | 0 |
|   | 0.1 | 22.4 | 4.2 | 32.9 |
|   | 1 | 32.6 | 5.2 | 58.0 |
|   | 10 | 27.6 | 7.0 | 69.9 |
| 4 | 0.1 | −9.4 | 5.2 | −10.9 |
|   | 1 | −1.3 | 3.2 | 14.7 |
|   | 10 | 24.2 | 5.6 | 37.7 |
| 6 | 0.1 | −11.8 | 3.8 | 29.7 |
|   | 1 | −11.8 | 4.1 | 15.1 |
|   | 10 | 10.1 | 4.4 | 26.6 |
| 9 | 0.1 | 19.5 | 4.7 | 31.7 |
|   | 1 | 43.9 | 7.3 | 52.0 |
|   | 10 | 56.1 | 22.9 | 73.0 |
| 11 | 0.1 | 2.8 | 14.9 | 33.4 |
|    | 1 | 17.7 | 14.4 | 61.7 |
|    | 10 | 22.3 | 10.1 | 62.3 |
| 13 | 0.1 | 33.3 | 7.7 | 44.4 |
|    | 1 | 12.5 | 7.6 | 72.0 |
|    | 10 | 25.0 | 5.5 | 75.2 |
| 15 | 0.1 | 6.3 | 5.3 | 72.7 |
|    | 1 | 16.7 | 4.8 | 69.9 |
|    | 10 | −2.0 | 5.3 | 72.1 |
| 20 | 0.01 | 16.7 | 5.3 | 24.3 |
|    | 0.1 | 19.0 | 4.9 | 23.0 |
|    | 1 | 45.2 | 10.7 | 52.0 |
| 22 | 0.1 | 48.8 | 3.1 | 43.8 |
|    | 1 | 35.1 | 3.7 | 65.5 |
|    | 10 | 41.8 | 1.2 | 63.0 |
| 24 | 0.1 | 34.9 | 4.8 | 28.2 |
|    | 1 | 42.3 | 7.1 | 56.1 |
|    | 10 | 50.5 | 5.3 | 55.7 |
| 26 | 0.1 | 13.0 | 3.5 | 12.2 |
|    | 1 | 23.7 | 4.6 | 51.3 |
|    | 10 | 14.4 | 5.2 | 52.8 |

TABLE 2

35-Day OVX

| Example No. | Dose (mg/kg) | Bone Mineral Content (% protected) | Uterine Weight (% increase vs. OVX) | Serum Cholesterol (% decrease vs. OVX) |
|---|---|---|---|---|
| 2 | 0.01 | −40 | 14.4 | 0.9 |
|   | 0.1 | −17.5 | 49.0 | 16.4 |
|   | 1.0 | −−7.5 | 71.2 | 30.7 |
|   | 10.0 | 50 | 73.5 | 48.2 |
| 4 | 0.01 | 10.7 | −1.0 | 2.3 |
|   | 0.1 | 14.7 | −4.8 | −37 |
|   | 1.0 | 41.3 | 74.8 | −24 |
|   | 10.0 | 54.2 | 83.3 | 51.3 |
| 6 | 0.01 | 6.7 | 13.4 | −1.5 |
|   | 0.1 | 10.0 | 16.2 | −15.8 |
|   | 1.0 | 0 | 27.6 | −11.6 |
|   | 10.0 | 40.0 | 77.6 | −2.0 |
| 20 | 0.01 | −2.1 | 38.6 | 45.0 |
|    | 0.1 | 20.8 | 89.2 | 42.6 |
|    | 1.0 | 12.5 | 78.4 | 57.7 |
|    | 10.0 | 25 | 90.6 | 53.6 |
| 22 | 0.01 | −24.4 | −2.3 | 9.2 |
|    | 0.1 | 6.7 | 55.0 | 31.9 |
|    | 1.0 | 44.4 | 48.4 | 53.5 |
|    | 10.0 | 42.2 | 48.8 | 59.5 |
| 24 | 0.01 | −24.4 | 4.2 | 19.9 |
|    | 0.1 | 33.3 | 40.0 | 30.6 |
|    | 1.0 | 31.1 | 81.6 | 49.6 |
|    | 10.0 | 64.4 | 42.0 | 50.5 |
| 26 | 0.01 | 0 | 1.3 | 0.5 |
|    | 0.1 | −29.2 | 41.1 | 39.4 |
|    | 1.0 | 54.2 | 96.9 | 51.8 |
|    | 10.0 | 50.0 | 62.5 | 45.0 |

TABLE 2-continued

35-Day OVX

| Example No. | Dose (mg/kg) | Bone Mineral Content (% protected) | Uterine Weight (% increase vs. OVX) | Serum Cholesterol (% decrease vs. OVX) |
|---|---|---|---|---|
| 28 | 0.01 | −0.6 | 13.4 | −6.1 |
|  | 0.1 | 42.7 | 61.8 | 10.4 |
|  | 1.0 | 22.1 | 80.8 | 4.4 |

TABLE 3

4-Day OVX

| Compound | Dose mg/kg | Uterine Wt. (% increase) | Eosinophil Peroxidose (Vmax) | Serum Cholesterol (% decrease) |
|---|---|---|---|---|
| [6-(methylsulfonoyloxy)-2-[4-(methylsulfonoyloxy)phenyl]benzo-[b]thien-3-yl][4-[2-(1-piperidinyl)ethoxy]-phenyl]methanone hydrochloride | 0.1 | −19.6 | 6.2 | 1.7 |
|  | 1.0 | −20.8 | 8.3 | 6.2 |
|  | 10.0 | −17.8 | 6.2 | 3.7 |
| [6-(phenylsulfonoyloxy)-2-[4-(phenylsulfonoyloxy)phenyl]benzo[b]thien-3-yl][4-[2-(1-piperidinyl)ethoxy]phenyl]-methanone hydrochloride | 0.1 | 20.9 | 4.8 | −6.8 |
|  | 1.0 | −7 | 3.6 | −0.2 |
|  | 10.0 | 27.9 | 4.9 | 6.1 |
| [6-(n-propylsulfonoyl)-2-[4-(n-propylsulfonoyl)phenyl]benzo[b]thien-3-yl][4-[2-(1-piperidinyl)ethoxy]phenyl]methanone, hydrochloride | 0.1 | −22.2 | 16.1 | −8 |
|  | 1.0 | −12.6 | 6.6 | 7.3 |
|  | 10.0 | 4.8 | 11.6 | 10.7 |
| [6-(n-heptylsulfonoyl)-2-[4-(n-heptylsulfonoyl)phenyl]benzo[b]thien-3-yl][4-[2-(1-piperidinyl)ethoxy]phenyl]methanone, hydrochloride | 0.1 | 2.9 | 3.6 | 11.6 |
|  | 1.0 | −2.6 | 4.0 | 9.9 |
|  | 10.0 | 3.5 | 3.5 | 13.5 |

TABLE 4

35-Day OVX

| Compound | Dose (mg/kg) | Bone Mineral Content (% protected) | Uterine Weight (% increase vs. OVX) | Serum Cholesterol (% decrease vs. OVX) |
|---|---|---|---|---|
| [6-(methylsulfonoyloxy)-2-[4-(methylsulfonoyloxy)phenyl]benzo-[b]thien-3-yl][4-[2-(1-piperidinyl)ethoxy]-phenyl]methanone hydrochloride | 0.01 | 2.8 | −17.7 | 4 |
|  | 0.1 | 5.6 | −10.5 | 3.6 |
|  | 1.0 | 2.8 | −13.4 | 2.6 |
|  | 10.0 | 5.6 | −7.9 | 3.5 |
| [6-(phenylsulfonoyloxy)-2-[4-(phenylsulfonoyloxy)phenyl]benzo[b]thien-3-yl][4-[2-(1-piperidinyl)ethoxyl]phenyl]-methanone hydrochloride | 0.01 | −35.3 | −6.4 | −10.8 |
|  | 0.1 | 5.9 | −7.7 | −14.4 |
|  | 1.0 | −17.6 | −9.9 | −19.0 |
|  | 10.0 | −50.0 | −29.4 | −15.5 |

DMBA-Inducted Mammary Tumor Inhibition

Mammary tumors were produced in femal Sprague-Dawley rats which were purchased from Harlan Industries, Indianapolis, Ind. At about 55 days of age, the rats received a single oral feeding of 20 mg of 7,12-dimethylbenz[a] anthracene (DMBA)- About 6 weeks after DMBA administration, the mammary glands were palpated at weekly intervals for the appearance of tumors. Whenever one or more tumors appeared, the longest and shortest diameters of each tumor were measured with a metric caliper, the measurements were recorded, and that animal was selected for experimentation. An attempt was made to uniformly distribute the various sizes of tumors in the treated and control groups such that average-sized tumors were equivalently distributed between test groups. Control groups and test groups for each experiment contained 5 to 9 animals. The average number of test animals is stated for each experiment in the data tables contained herein.

Test compounds were administered either through intraperitoneal injections in 2% acacia, or orally. Orally administered compounds were either dissolved or suspended in 0.2 mL corn oil. Each treatment, including acacia and corn oil control treatments, was administered once daily to each test animal. Following the initial tumor measurement and selection of test animals, tumors were measured each week by the above-mentioned method. The treatment and measurements of animals continued for 3 to 5 weeks at which time the final areas of the tumors were determined. For each compound and control treatment, the change in the mean tumor area was determined. The mean change was analyzed for its significance, using Student's t-test.

We claim:

1. A compound of the formula

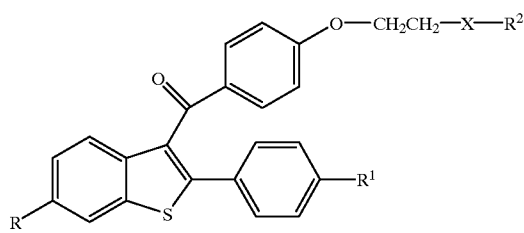

where

X is a bond or —$CH_2$—;

$R^2$ is piperidino;

R is OH, —$OSO_2$—$(CH_2)_n$—$CH_3$ or

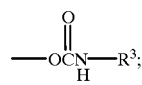

$R^1$ is hydrogen, OH, fluoro, chloro, —$OSO_2$—$(CH_2)_n$—$CH_3$ or

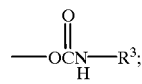

each $R^3$ is independently $C_1$-$C_6$ alkyl, $C_3$-$C_6$ cycloalkyl, unsubstituted or substituted phenyl where the substituent is fluoro, chloro, $C_1$-$C_3$ alkyl or $C_1$-$C_3$ alkoxy;

each n is independently 3, 4 or 5; and pharmaceutically acceptable salts and solvates thereof; provided that at least one of R and $R^1$ is

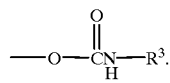

2. A compound of claim 1 where R is —$OSO_2$—$(CH_2)_n$—$CH_3$.

3. A pharmaceutical composition comprising a pharmaceutically acceptable carrier, diluent or excipient and a compound having the formula

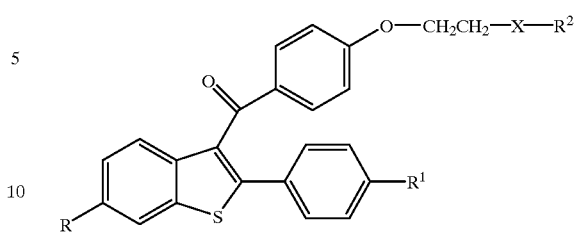

where

X is a bond or —$CH_2$—;

$R^2$ is piperidino;

R is OH, —$OSO_2$—$(CH_2)_n$—$CH_3$ or

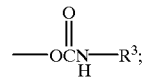

$R^1$ is hydrogen, OH, fluoro, chloro, —$OSO_2$—$(CH_2)_n$—$CH_3$, or

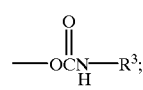

each $R^3$ is independently $C_1$-$C_6$ alkyl, $C_3$-$C_6$ cycloalkyl, unsubstituted or substituted phenyl where the substituent is fluoro, chloro, $C_1$-$C_3$ alkyl or $C_1$-$C_3$ alkoxy;

each n is independently 3, 4 or 5; and pharmaceutically acceptable salts and solvates thereof; provided that at least one of R and $R^1$ is

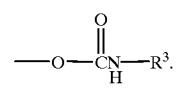

4. A pharmaceutical composition of claim 3 where R is —$OSO_2$—$(CH_2)_n$—$CH_3$.

5. A method of inhibiting bone loss comprising administering to a human in need of treatment an effective amount of a compound having the formula

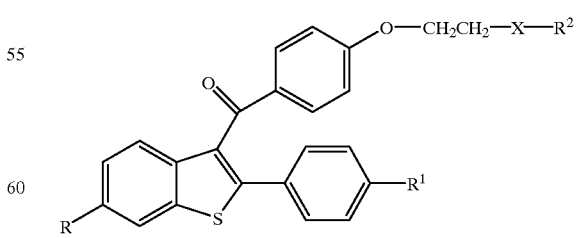

where

X is a bond or —$CH_2$—;

$R^2$ is piperidino;

R is OH, —OSO$_2$—(CH$_2$)$_n$—CH$_3$ or

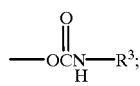

R$^1$ is hydrogen, OH, fluoro, chloro, —OSO$_2$—(CH$_2$)$_n$—CH$_3$, or

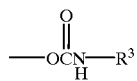

each R$^3$ is independently C$_1$–C$_6$ alkyl, C$_3$–C$_6$ cycloalkyl, unsubstituted or substituted phenyl where the substituent is fluoro, chloro, C$_1$–C$_3$ alkyl or C$_1$–C$_3$ alkoxy;

each n is independently 3, 4 or 5; and pharmaceutically acceptable salts and solvates thereof; provided that at least one of R and R$^1$ is

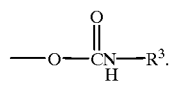

6. A method of claim 5 where R is —OSO$_2$—(CH$_2$)$_n$—CH$_3$.

7. A method of lower serum cholesterol levels comprising administering to a human in need of treatment a serum cholesterol lowering amount of a compound having the Formula

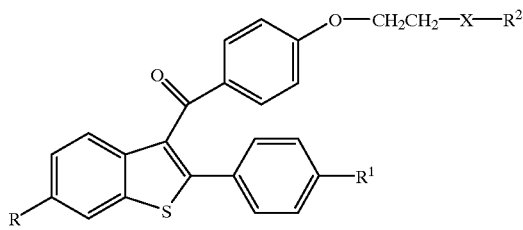

where

X is a bond or —CH$_2$—;
R$^2$ is piperidino;
R is OH, —OSO$_2$—(CH$_2$)$_n$—CH$_3$ or

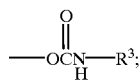

R$^1$ is hydrogen, OH, fluoro, chloro, —OSO$_2$—(CH$_2$)$_n$—CH$_3$, or

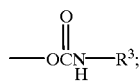

each R$^3$ is independently C$_1$–C$_6$ alkyl, C$_3$–C$_6$ cycloalkyl, unsubstituted or substituted phenyl where the substituent is fluoro, chloro, C$_1$–C$_3$ alkyl or C$_1$–C$_3$ alkoxy;

each n is independently 3, 4 or 5; and pharmaceutically acceptable salts and solvates thereof; provided that at least one of R and R$^1$ is

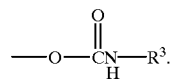

8. A method of claim 7 where R is —OSO$_2$—(CH$_2$)$_n$—CH$_3$.

9. A method of treating hormone dependent breast or uterine carcinoma comprising administering to a human in need of treatment an effective amount of a compound having the Formula

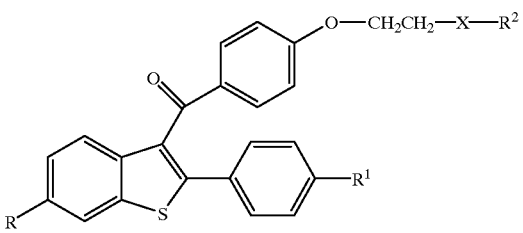

where

X is a bond or —CH$_2$—;
R$^2$ is piperidino;
R is OH, —OSO$_2$—(CH$_2$)$_n$—CH$_3$ or

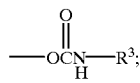

R$^1$ is hydrogen, OH, fluoro, chloro, —OSO$_2$—(CH$_2$)$_n$—CH$_3$, or

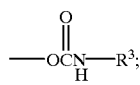

each R$^3$ is independently C$_1$–C$_6$ alkyl, C$_3$–C$_6$ cycloalkyl, unsubstituted or substituted phenyl where the substituent is fluoro, chloro, C$_1$–C$_3$ alkyl or C$_1$–C$_3$ alkoxy;

each n is independently 3, 4 or 5; and pharmaceutically acceptable salts and solvates thereof; provided that at least one of R and R$^1$ is

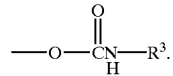

10. A method of claim 9 where R is —OSO$_2$—(CH$_2$)$_n$—CH$_3$.

* * * * *